United States Patent
Gaft et al.

(10) Patent No.: US 9,891,173 B2
(45) Date of Patent: Feb. 13, 2018

(54) METHOD OF LASER-INDUCED BREAKDOWN SPECTROSCOPY IN AIR

(71) Applicant: LASER DISTANCE SPECTROMETRY, Petach Tikva (IL)

(72) Inventors: Michael Gaft, Rishon Lezion (IL); Lev Nagli, Petach Tikva (IL)

(73) Assignee: LASER DISTANCE SPECTROMETRY LTD., Petach, Tikva (IL)

( * ) Notice: Subject to any disclaimer, the term of this patent is extended or adjusted under 35 U.S.C. 154(b) by 85 days.

(21) Appl. No.: 14/894,037

(22) PCT Filed: May 29, 2014

(86) PCT No.: PCT/IL2014/050484
§ 371 (c)(1),
(2) Date: Nov. 25, 2015

(87) PCT Pub. No.: WO2014/191999
PCT Pub. Date: Dec. 4, 2014

(65) Prior Publication Data
US 2016/0116415 A1    Apr. 28, 2016

Related U.S. Application Data

(60) Provisional application No. 61/828,751, filed on May 30, 2013.

(51) Int. Cl.
*G01J 3/30* (2006.01)
*G01N 21/71* (2006.01)
(Continued)

(52) U.S. Cl.
CPC ............ *G01N 21/718* (2013.01); *G01J 3/443* (2013.01); *G01J 3/4412* (2013.01); *G01N 2201/06113* (2013.01)

(58) Field of Classification Search
CPC ......... G01N 21/718; G01N 2201/06113; G01J 3/4412; G01J 3/443
(Continued)

(56) References Cited

U.S. PATENT DOCUMENTS 4,925,307 A    5/1990    Cremers et al.
6,008,897 A    12/1999   Sabsabi et al.
(Continued)

FOREIGN PATENT DOCUMENTS

CN    102507512 A    6/2012
CN    102841078 A    12/2012
(Continued)

OTHER PUBLICATIONS

Yang et al. "Mid-Infrared Atomic and Molecular Laser-Inducted Breakdown Spectroscopy Emissions from Solid Substances", Optical Society of Ameria, 2009.*
(Continued)

*Primary Examiner* — Hina F Ayub
(74) *Attorney, Agent, or Firm* — Sughrue Mion, PLLC

(57) ABSTRACT

A method for detecting an element in a sample using molecular emission by double pulse laser-induced breakdown spectroscopy is provided. The method includes observing emissions from molecules including the element to be detected. The method is particularly useful for detecting halogens, whose elemental emissions are difficult to detect, rare earth elements and boron.

20 Claims, 15 Drawing Sheets

(51) Int. Cl.
*G01J 3/443* (2006.01)
*G01J 3/44* (2006.01)

(58) Field of Classification Search
USPC .......................................................... 356/318
See application file for complete search history.

(56) References Cited

U.S. PATENT DOCUMENTS

| | | | |
|---|---|---|---|
| 6,034,768 | A | 3/2000 | Fraser et al. |
| 8,319,964 | B2 | 11/2012 | Worthington |
| 2002/0093653 | A1* | 7/2002 | Detalle ................ G01N 21/718 356/318 |
| 2011/0109904 | A1* | 5/2011 | Ugolin ............... G01N 21/6452 356/311 |

FOREIGN PATENT DOCUMENTS

| | | |
|---|---|---|
| CN | 202916196 U | 5/2013 |
| EP | 1223423 A2 | 7/2002 |
| EP | 1416265 | 5/2004 |
| WO | 2014/191999 A1 | 12/2014 |

OTHER PUBLICATIONS

An International Search Report and a Written Opinion both dated Sep. 22, 2014, which issued during the prosecution of Applicant's PCT/IL2014/050484.

An International Preliminary Report on Patentability dated Dec. 1, 2015, which issued during the prosecution of Applicant's PCT/IL2014/050484.

An English Translation of an Office Action dated Mar. 31, 2016, which issued during the prosecution of Russian Patent Application No. 2015156323.

Bernath, P. et al. "Laser Spectroscopy of CaBr." Journal of Molecular Spectroscopy, No. 88, (1981), pp. 175-193, [retrieved on Nov. 8, 2014]. Retrieved from the Internet <URL:http://bernath.uwaterloo.ca/media/5.pdf>.

Niki, H. et al. "Measurement technique of Boron Isotopic Ratio by Laser-induced Breakdown Spectroscopy". Journal of Nuclear Science and Technology, vol. 35. No. 1. pp. 34-39, Jan. 1998. [retrieved on Nov. 8, 2014], Retrieved from the Internet <URLhttp://www.tandfonline.com/doi/pdf/10.1080/18811248.1998.9733817>.

U.S. Appl. No. 61/828,751, filed May 30, 2013.

An Office Action together with the English translation dated Jul. 3, 2017 which issued during the prosecution of Chinese Patent Application No. 201480041306.X.

Dimitra N. Stratis, Kristine L. Eland, and S. Michael Angel, "Dual-Pulse LIBS Using a Pre-ablation Spark for Enhanced Ablation and Emission," Appl. Spectrosc. 54, 1270-1274 (2000).

An Office Action together with the English translation dated Oct. 18, 2017 which issued during the prosecution of Russian Patent Application No. 2015156323.

* cited by examiner

METHOD OF LASER-INDUCED BREAKDOWN SPECTROSCOPY IN AIR

CROSS-REFERENCE TO RELATED APPLICATION

This is a National Stage of International Application No. PCT/IL2014/050484 filed May 29, 2014, claiming priority based on U.S. Provisional Patent Application Ser. No. 61/828,751, filed May 30, 2013 and entitled METHOD OF ELEMENTAL ANALYSIS USING MOLECULAR EMISSION BY LASER-INDUCED BREAKDOWN SPECTROSCOPY IN AIR, the disclosure of which is hereby incorporated by reference and priority of which is hereby claimed pursuant to 37 CFR 1.78(a)(4) and (5)(i).

FIELD OF THE INVENTION

The present invention relates to a method for detecting elements difficult to detect by their ion line spectra in Laser-Induced Breakdown Spectroscopy (LIBS) using molecular emissions.

BACKGROUND OF THE INVENTION

Various techniques are known for detecting elements in a sample using laser-induced breakdown spectroscopy.

SUMMARY OF THE INVENTION

The present invention seeks to provide a method for detecting elements difficult to detect by their ion line spectra in Laser-Induced Breakdown Spectroscopy (LIBS) using molecular emissions.

There is thus provided in accordance with a preferred embodiment of the present invention a method for detecting an element in a sample, the method including: providing a laser-induced breakdown spectroscopy (LIBS) system including: a first laser, a second laser, a spectrometer and a detector, emitting a first pulse from the first laser to the sample; thereafter emitting a second pulse from the second laser to the sample; and detecting molecular emissions of a molecule including the element.

In accordance with a preferred embodiment of the present invention, the element is a halogen. In one embodiment, the element is F. Preferably, the molecule is selected from CaF, MgF, BaF and SrF. More preferably, the molecule is selected from CaF and MgF. In an alternative embodiment, the element is Cl. Preferably, the molecule is selected from CaCl, MgCl, SrCl and BaCl. More preferably, the molecule is selected from CaCl, MgCl, and SrCl. In a further alternative embodiment, the element is Br. Preferably, the molecule is CaBr. In an additional alternative embodiment, the element is I. Preferably, the molecule is CaI.

In accordance with another preferred embodiment of the invention, the element is a rare-earth element. Preferably, the element is selected from Y, La and Th. More preferably, the element is selected from Y and La. Preferably, the molecule is selected from YO and LaO. In accordance with another preferred embodiment of the invention, the element is boron. Preferably, the molecule is BO, $BO_2$, a molecule consisting of boron, calcium and oxygen, or a molecule consisting of boron, magnesium and oxygen.

In accordance with a preferred embodiment of the present invention, the time between the emitting a first pulse and the emitting a second pulse is 300-1000 ns. Preferably, both of the first laser and the second laser are Nd:YAG lasers.

Preferably, the detecting begins after a delay time following the emitting a second pulse. The delay time is preferably 5-75 µs, more preferably 5-50 µs, and most preferably 5-30 µs.

In accordance with a preferred embodiment of the present invention, the sample is in a stationary position in the LIBS system. In accordance with an alternative preferred embodiment of the present invention, the sample is on a moving conveyer belt.

BRIEF DESCRIPTION OF THE DRAWINGS

The present invention will be understood and appreciated more fully from the following detailed description, taken in conjunction with the drawings in which.

DETAILED DESCRIPTION OF THE INVENTION

Figure 1:
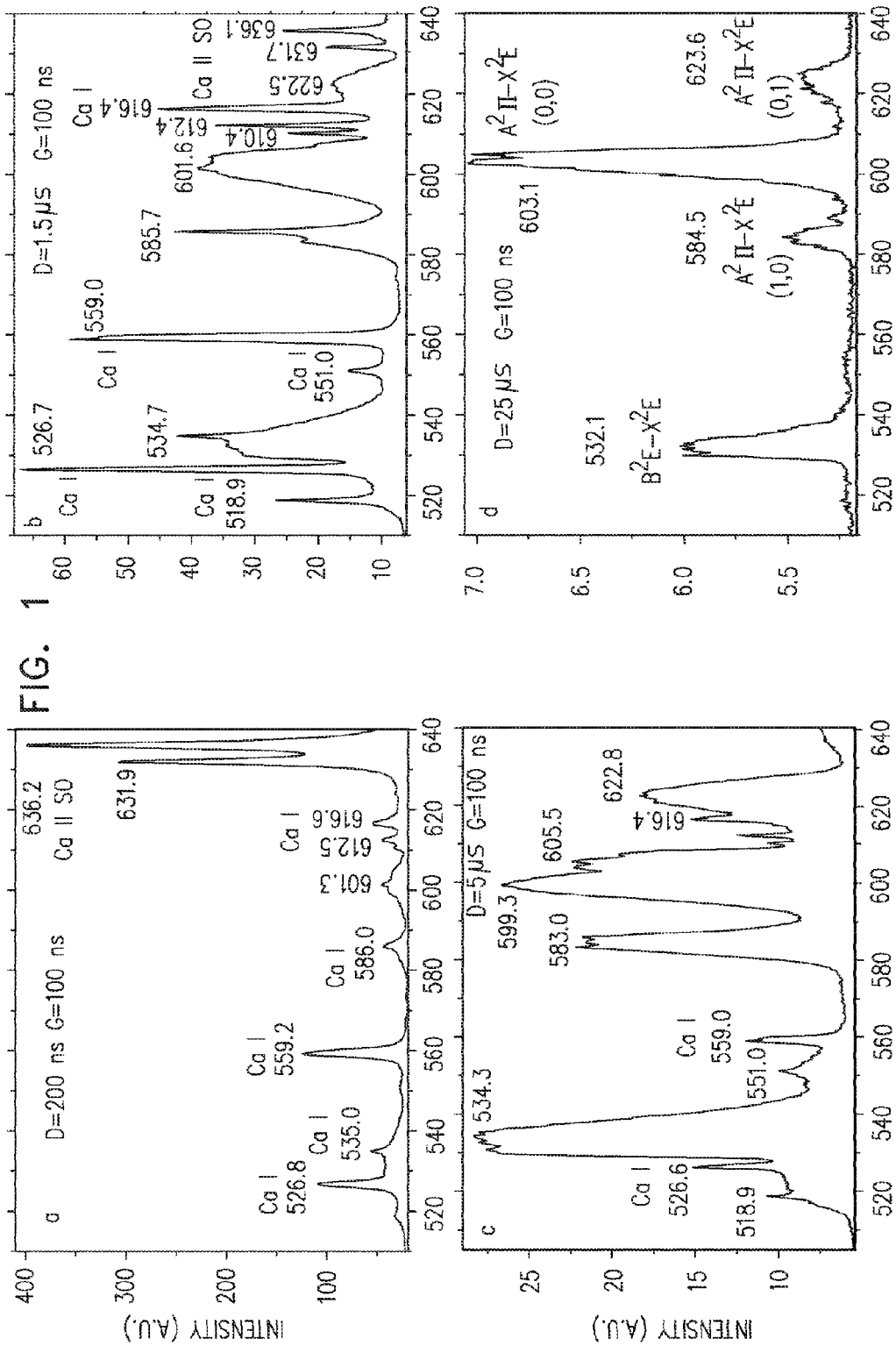
FIGS. 1, 2, 3, 4, 5, 6, 7, 8, 9, 10, 11, 12, 13, 14 and 15 are graphical depictions of spectroscopic data obtained by a method in accordance with a preferred embodiment of the present invention.

Laser Induced Breakdown Spectroscopy (LIBS) uses optical emission spectra of atoms and atomic ions to analyze solid, liquid and gaseous samples. It offers ideal characteristics for real-time elemental analysis at atmospheric pressure, including remote applications. With LIBS, a small portion of a sample is converted to plasma by use of a laser, and the emission of the elements in the plasma is measured.

While there are abundant LIBS applications involving analysis of metallic elements in various samples (alloys, soil, paper, paint, etc.), non-metals such as halogens, have been less investigated. Efficient quantitative detection for halogens is necessary in a wide range of applications, specifically for online control of minerals in the phosphate and potash fertilizer industries. The difficulty for halogen determination by LIBS is attributed to, among other reasons, their energy level distribution. For example, the strongest emission lines for fluorine and chlorine lie in the VUV spectral range (95.5 and 134.7 nm for F and Cl, respectively). Detection capabilities in this region are limited by atmospheric and materials absorption, as well as detector sensitivity.

Optical transitions applicable for LIBS detection but less strong than those in the VUV exist in the visible and in the near IR (500-850 nm). These are transitions between the excited states $(n+1)s\ ^4P-(n+1)p\ ^4D$ manifold (n=2 for F and n=3 for Cl), corresponding to wavelengths centered around 685.6 nm for F, and 837.6 nm for Cl. Detection in this spectral region is more amenable compared to the VUV region but have upper levels 10.40 and 14.50 eV, respectively, above the ground state (Cremers, Miziolek). Nevertheless, the detection limits for these lines are less than satisfactory for demanding applications. The following optimal conditions for F and Cl detection were determined: an intensified and gated CCD detector with improved spectral response in NIR; the third harmonic of the Nd:YAG laser (355 nm) for plasma creation, it is possible to enhance the sensitivity to halogens by producing the plasma in a inert gas atmosphere with a pressure range of inert gas below 100 mbar (Miziolek).

One of the potential ways to improve plasma analysis sensitivity for halogens is to use molecular emission bands and not elemental emission lines. Simple molecules are sometimes formed as atoms recombine in the cooling plasma. Jaffe discloses molecular emission spectra for BaBr, BaCl, CaCl and CaF, as well as various oxide molecules produced using arc induced plasma. Arc plasma differs from LIES in that the plasma temperature in arc plasma is about 5000 K, while the plasma temperature in LIBS is about 50,000 K. In addition, arc plasma analysis may only be performed in a laboratory, while LIES may be carried out in the field. Emission spectra for BeF and MgF (Pelegrini) and MgCl (Darji) have also been observed.

In another related technique Laser Ablation Molecular Isotopic Spectrometry (LAMIS), isotopic analysis of strontium molecules was performed (Mao). Emission spectra of SrO and diatomic halides of strontium SrF, SrCl, SrBr and SrI were measured in order to differentiate between the different isotopes of strontium. It was found that SrO and SrF are particularly useful for this purpose. SrF was formed from a pure sample of $SrF_2$. This technique was not used to detect fluorine or any other element in a natural or artificial sample (Mao).

In addition to halogens, it was found that certain rare-earth elements exhibit molecular emission in arc plasma. For example, while Y is readily observable in arc plasma, the molecular emissions from YO made possible the detection of yttrium in apatite with a usual concentration less than 0.5%. In other minerals, yttrium has been detected in concentrations as low as 0.01%. In the case of lanthanum, its traces have been detected in apatite, where it commonly occurs in concentrations of less than 0.1%, by observing the emission from LaO (Peterson).

In addition to halogens and rare-earth elements, it was found that boron exhibits molecular emission in arc plasma. For example, BO and $BO_2$ exhibit multiple emission bands in UV-visible parts of the spectrum (Pearse). LAMIS isotopic analysis using the UV band of BO peaking at 255 nm was also performed (Russo).

One of the advantages of detecting emission of molecules is their long plasma life time. Thus they may be detected after a long delay time when nearly all emissions of atoms and ions are already quenched. This is particularly important for applications wherein strong interfering emissions from different atoms and ions exist. One of the main interfering atoms is Fe. Molecular emission enables detection of B in B—Fe bearing ores much better than atomic or ionic emissions.

One option for improving LIBS sensitivity is to use double-pulse (DP) LIBS. In DP-LIBS, two laser pulses are fired at the sample with a certain time difference between pulses. Use of DP-LIBS results in increased emission intensity and, therefore, increased sensitivity for the elements in question. It has been surprisingly discovered that the increase in signal intensity for molecules in DP mode is much greater than the increase in signal intensity for atoms. DP mode is thus especially suitable for the detection of elements, specifically halogens, difficult to detect in LIBS, by observing molecular emission bands. Using DP mode, the sensitivity of molecule detection is approximately 100-200 times higher as compared to ion detection, in particular for elements F, Cl and La.

In accordance with a first embodiment of the present invention, there is provided a method for detecting elements in a sample using molecular emission by laser-induced breakdown spectroscopy (LIBS), the method comprising providing a LIBS system including a double-pulse laser, a spectrometer and a detector, providing a sample comprising an element, or elements, of interest, and performing LIBS on the sample and observing the emissions of a molecule comprising the element of interest.

The laser may be a single laser capable of producing two pulses within about 1 µs of each other. Alternatively, the double-pulse laser may include a pair of lasers operating at similar output energy levels. Preferably, the lasers output at a wavelength of about 1064 nm, although other wavelengths may be used. For example, the lasers may be Nd:YAG lasers operated with the first, second, third or fourth harmonic having a wavelength of 1064, 532, 355 and 266 nm, respectively. In a preferred embodiment, the laser is an Nd:YAG twin system purchased from Quantel (Les Ulis, France).

The laser energy is preferably from 10-200 mJ/pulse and more preferably 20-50 mJ/pulse. The pulse duration is preferably from 6-8 ns, preferably 8 ns. The delay between the two pulses is preferably 100-10,000 ns, more preferably 300-1000 ns.

The laser pulse may be focused onto the surface of the sample using a lens, such as a quartz lens. The laser spot diameter is preferable from 100-500 µm, more preferably 300 µm. The pulse energy fluence is preferably from 5-100 $J/cm^2$, more preferably from 15-50 $J/cm^2$.

The spectrometer may be any spectrometer that has suitable sensitivity and spectral resolution. The spectrometer preferably has a diffraction grating with 300-2400 lines/mm, more preferably 1200 or 2400 lines/mm. In a preferred embodiment, the spectrometer is a Shamrock SR 303i-A spectrograph purchased from Andor Technology (Belfast, UK). The plasma emissions are preferably guided to the spectrometer using an optical fiber, having a numerical aperture suitable for the corresponding spectrometer, preferably a numerical aperture of 0.22.

The detector may be any detector that has suitable sensitivity and gating ability. For example, the detector may be an intensified charge-coupled device (ICCD) camera. In a preferred embodiment the detector is an iStar DH-720 25F-03 camera purchased from Andor Technology (Belfast, UK). The delay time is from 1 ns-19 ms, preferably 5-50 µs, and the gate width is preferably from 10-50 µs. Another example is gated AvaSpec spectrometer with charge-coupled device (CCD) camera. The delay time is from 100 ns, and the gate width is 1 ms.

The element of interest is preferably a halogen, a rare earth element or boron. The halogen is preferably F, Cl, Br or I, more preferably F, Cl or Br and most preferably F or Cl. The rare earth element is preferably Y, La or Th, most preferably Y or La. For the following elements it was found that molecular emission is not substantially better than the ion emission: Ti, Pb, Si, Mn, Al, Zr, Fe, Ca, Mg, B, S, Zn, K, Na and P.

When the element of interest is F, the molecule is preferably selected from CaF, MgF, SrF and BaF, more preferably CaF and MgF. When the element of interest is Cl, the molecule is preferably selected from CaCl, MgCl, BaCl and SrCl, more preferably CaCl, MgCl, and SrCl. When the element of interest is Br, the molecule is preferably selected from CaBr, BaBr and SrBr, most preferably CaBr. When the element of interest is I, the molecule is preferably selected from CaI, BaI and SrI, most preferably CaI. When the element of interest is a rare earth element, the molecule is preferably an oxide, most preferably YO or LaO. When the element of interest is B, the molecule is preferably selected from BO, $BO_2$, $Ca_xB_yO_z$ or $Mg_xB_yO_z$. Table 1 sets forth the wavelengths at which the molecules emit energy.

TABLE 1

| Molecule | Emission wavelengths (nm) | Source |
|---|---|---|
| CaF | 532.1, 584.5, 603.1, 623.6 | Peterson, Oujja |
| BaF | 496.5, 501.0, 513.7, 686.4, 696.2, 714.4, 743.2 | Jenkins, 1932 |
| MgF | 262.8, 268.0, 273.5, 348.2, 358.0, 365.6 | Jenkins, 1934 |
| CaCl | 606.8, 618.8, 631.4 | Berg |
| MgCl | 359.2, 369.0, 375.8, 381.2, 382.8 | Pearse |
| SrCl | 594.7, 597.5, 605.9, 623.1, 634.7, 645.6, 660.1, 673.0, 682.5 | Pearse |
| CaBr | 625-628 | Pearse |
| LaO | 435-450, 535-550, 565-575, 730-750, 775-815 | Pearse |
| YO | 616.5, 614.8, 613.2, 600.3, 598.7, 597.2 | Pearse |
| BO, α system | 367.9, 384.9, 436.3, 461.2, 461.5 | Pearse |
| $BO_2$ | 471.0, 493.0, 518.0, 545.0, 580.0, 603.0, 620.0, 639.0 | Pearse |
| $Ca_xB_yO_z$ | 563.3, 594.6 | Determined herein |
| $Mg_xB_yO_z$ | 355.3, 368.9, 373.2 | Determined herein |

When the element of interest is a halogen, the sample is preferably a natural mineral containing both halogen and Ca, Mg, Ba or Sr, mainly Ca, such as fluorite $CaF_2$, apatite $Ca_5(PO_4)_3F$, and apophyllite $KCa_4Si_8O_{20}F\times8H_2O$. Alternatively, the sample may be a mixture of several natural minerals, one of which contains a halogen, such as cryolite $Na_3AlF_6$, topaz $Al_2SiO_4(OH,F)$, sylvite KCl, halite NaCl, and another of which contains Ca, Mg, Ba or Sr, preferably Ca and Mg, such as calcite $CaCO_3$ and dolomite $MgCO_3$. In one embodiment, the sample is an extraterrestrial sample. Alternatively, the sample may be a manmade material such as concrete. Concrete contains a large quantity of calcium, and thus CaCl molecular emission is a potential tool for Cl quantitative analysis in concrete. In another preferred embodiment, the sample is a chemically pure compound preferably selected from $CaF_2$, $BaF_2$, $MgF_2$, $CaCl_2$, $MgCl_2$, $SrCl_2$, $CaBr_2$, $MgBr_2$, $SrBr_2$, $CaI_2$, $MgI_2$, and $SrI_2$ and their mixtures.

When the element of interest is a rare-earth element, the sample is preferably a natural mineral containing at least one of La, Y and Th. In a preferred embodiment, the mineral is bastnasite $(Ce,La)CO_3(F,OH)$, xenotime $YPO_4$, or monazite $(Ce,La,Nd,Th)(PO_4,SiO_4)$. When the element of interest is boron, the sample is preferably a natural mineral containing boron. Preferably, the sample is a mineral containing boron and calcium, such as danburite $CaB_2(SiO_4)_2$, or boron and magnesium, such as boracite $Mg_3B_7O_{13}Cl$. Since atoms and ions in the plasma are short-lived while molecules exist for a longer period of time, collection of the emission spectra is preferably delayed with respect to the firing of the lasers. The delay time is preferably from 5 μs to 75 μs, preferably 5 μs to 50 μs, and more preferably 5-30 μs.

In some embodiments, the LIBS system is calibrated for one or more elements, and the amount of each element in the sample is quantified. Detection by molecules is preferential not only for low concentrations of the corresponding elements. In samples wherein the concentration of an element is high, the system may become saturated and quantification using an elemental peak is difficult. Molecular emission peaks appear to have a higher saturation threshold than elemental emission peaks, such that quantifications that are not possible using elemental peaks may be possible using molecular peaks.

In one embodiment of the present invention, the method is carried out in a laboratory. In an alternative embodiment, the method is carried out in the field.

In one embodiment of the present invention, the method is carried out as a batch process, wherein each individual sample is placed in a stationary position in the LIBS system for analysis. In an alternative embodiment, the method is an online method, wherein the samples are moving on a conveyer belt. The system for carrying out the online method may be the system described in PCT/IL2012/000225 filed Jun. 7, 2012, published as WO 2012/168938 on Dec. 13, 2013 and entitled "METHOD AND APPARATUS FOR QUANTITATIVE ANALYSIS OF SAMPLES BY LASER INDUCED PLASMA (LIP)" the contents of which are hereby incorporated herein by reference in their entirety.

EXAMPLES

LIBS was performed using a confocal Single Pulsed (SP) or Double Pulsed (DP) plasma configuration. The system consisted of a double pulse Nd:YAG laser (Quantel twin system containing two Big Sky Ultra 50 lasers, 1.06 μm, maximal energy 50 mJ/pulse, duration 8 ns). A maximum energy of 3-50 mJ for the first laser pulse and 50 mJ for the second laser pulse were used. A delay generator controlled the timing of laser pulses such that the time between the two laser pulses was 300-10000 ns. The laser beams were focused through a 25 cm focusing quartz lens located about 20 cm above the sample. The laser spot diameter was determined by the knife-edge method and was about 300 μm on the sample surface, such that 10 mJ of pulse energy provided 15 $J/cm^2$ fluence. The emitted plasma radiation was collected by a 0.22 NA optical fiber and guided to a Shamrock SR 303i-A spectrometer (Andor, Belfast, UK) equipped with 1200 and 2400 lines/mm diffraction gratings. The spectrometer calibration with respect to wavelength and to spectral resolution was checked by measuring low pressure Hg lamp line position and width. For a spectrometer slit of 10 μm the spectral resolutions were 0.1 nm for the 2400 l/mm grating and 0.16 nm for the 1200 l/mm grating (measured as FWHM on Hg 256 nm line). The detector was an DH-720 25F-03 intensified charge-coupled device (ICCD) camera (Andor, Belfast, UK). Time resolution of the ICCD camera was determined by analyzing the temporal profile of the laser pulse using the second harmonic of Nd-YAG. It was found that using the kinetic series technique with a gate width and step of 1 ns, the measured FWHM of the laser pulse was 4-7 ns, which corresponds to its tabulated value (4 ns). The persistence data were measured by kinetic series modes with different delay and gate width parameters. The time interval of 500 ns was used (100 points with 5 ns steps).

In some experiments, the spectrometer was an AvaSpec industrial delayed-integration CCD spectrometer (Avantes, Apeldoorn, Netherlands) with a spectral resolution of 0.5 nm. The fixed integration time was 1 ms, and the variable delay started from 100 ns.

The samples were mounted on a moving holder so that every laser shot was delivered to a fresh spot on the sample surface. The line intensities in the figures are presented in arbitrary units (a.u.), which are comparable inside each figure, but not comparable between different figures.

Example 1—CaF

FIG. 1 presents SP LIBS emissions of natural fluorite $CaF_2$ and its time evolution with different delay times and gate width of 100 ns. With short delay time of 200 ns (FIG. 1a) the spectrum contains mainly narrow emission lines accompanied by very weak several relatively broad spectral bands. The lines at 526.8, 535.0, 559.2, 586.0, 612.5 and 616.6 nm may be readily assigned to neutral Ca I atoms, while the lines at 636.2 and 631.9 nm are the second order lines of Ca II ions peaking at 316.0 and 318.0 nm (NIST and Smith). After a delay of 1.5 µs, Ca II ions have decreased and the Ca I atoms lines and remaining bands dominate the spectrum (FIG. 1b). After delay of 5.0 µs the Ca I atom lines nearly totally disappear and only the bands peaking at 534.3, 583.0, 600.0-605.5, and 622.8 remain (FIG. 1c). After delay of 25 µs the lines totally disappear and only the bands at 532.1, 584.5, 603.1 and 623.6 nm present. The relative intensities of those bands differ from the previous graph with less delay, namely the band at 603.1 nm is the strongest one, while other bands are relatively less intensive (FIG. 1d). The bands in FIG. 1d are much less studied in LIBS compared to the Ca ion emission lines, but they are well known in arc induced plasma. The band peaking at 532.1 nm has been ascribed to the green $B^2\Sigma$-$X^2\Sigma$ system, while the bands peaking at 584.5, 603.1 and 623.6 nm are ascribed to orange $A^2\Pi$-$X^2\Sigma$ systems of the diatomic CaF molecule (Peterson and Oujja).

The temporal evolution of the $CaF_2$ plume was measured by kinetic series method by measuring the intensity of emissions as a function of the delay between the plasma formation and the opening of the acquisition temporal gate. The emission of Ca II decays very fast with decay time of approximately 140-150 ns, while the emission of Ca I decays more slowly with decay time of approximately 700 ns. The molecular emission of CaF is temporally broader as compared to the ionic species. It reaches its maximum after approximately 800 ns followed by a decay with a decay time of 4-6 µs. It corresponds well to this band's behavior in ablation plasma where it has a temporal plateau in the 400-600 ns interval (Oujja). Thus those bands persist after a relatively long delay time of several microseconds while the ion line emission is mostly quenched.

The CaF bands were characterized by different plasma temporal evolution. It was found that decay of the band at 532.1 nm may be approximated by two exponents with decay times of 1.1 and 4.5 µs, at 584.5 nm by one exponent with decay time of 4.0 µs, at 603.1 nm by two exponents with decay times of 1.1 and 6.2 µs and at 623.6 nm by one exponent with decay time of 4.5 µs. The longest decay component of the band at 603.1 nm explains its relative persistence in the spectra with longer delay time. This decay is three orders of magnitude longer compared to the radiative lifetime of vibronic levels of the $B^2\Sigma$-$X^2\Sigma$ state for different molecules, including CaF (Oujja). Thus decay time is connected to the duration of the life of those molecules in plasma plume.

Figure 2:
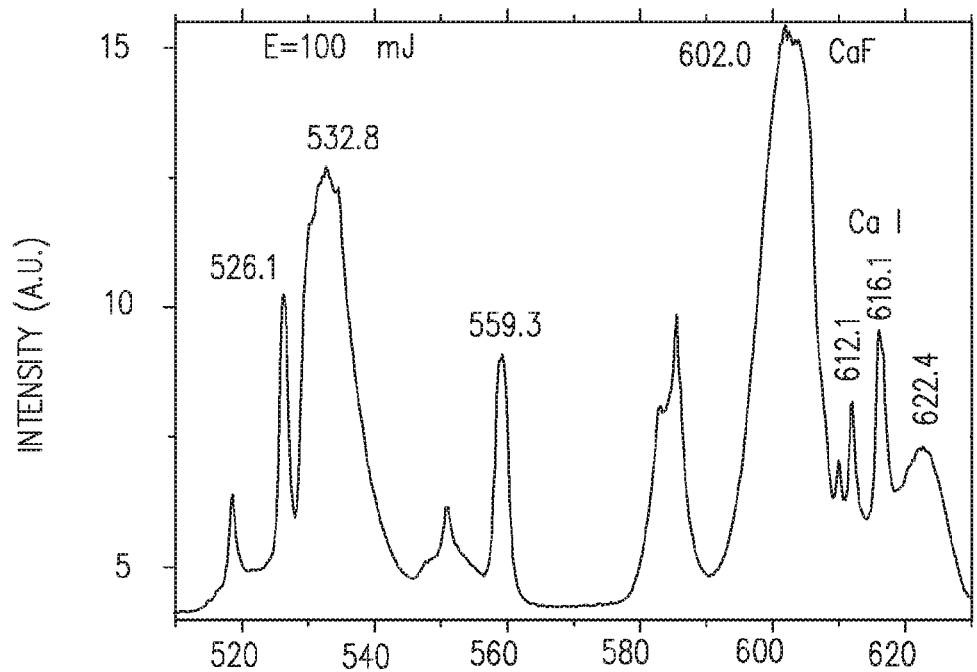
Figure 2:
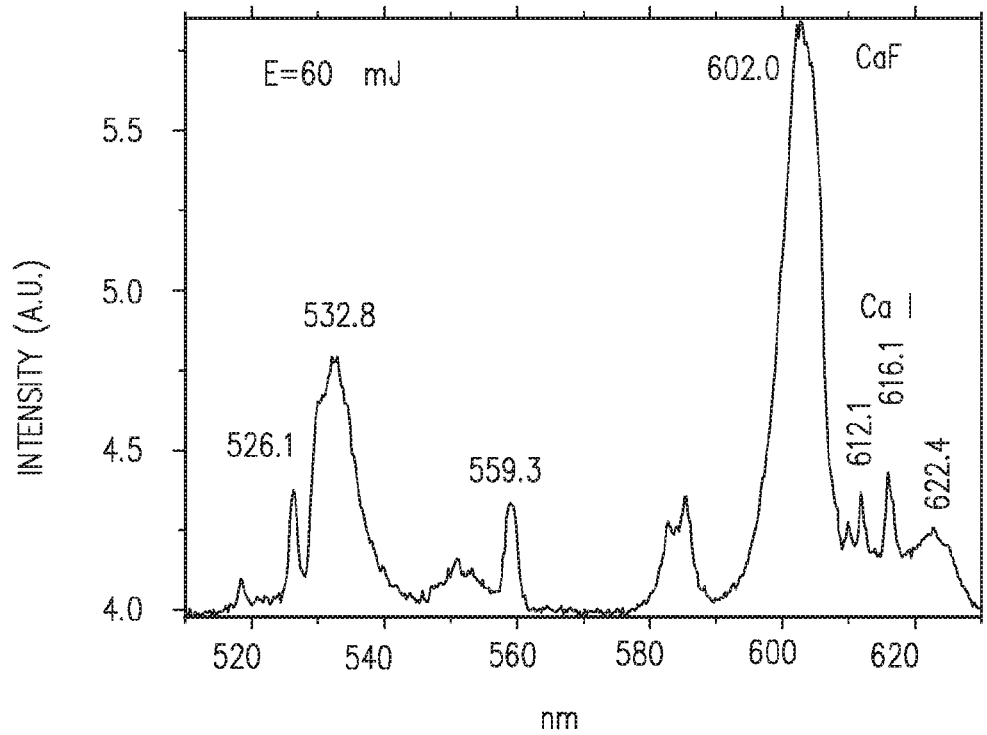

The intensity of molecular emission bands is less dependent on excitation laser energy than that of ion emission lines. As shown in FIG. 2, when the laser energy is 100 mJ (upper panel), the intensity ratio between the CaF molecular band at 602.0 nm and the Ca I ion line at 616.1 nm is approximately 1.8, while with a laser energy of 60 mJ (lower panel), and the corresponding diminishing of excitation density, this ratio is approximately 9.0.

The lower dependency of molecular peaks on laser intensity is very important for online LIBS applications, where the sample surface very often is not exactly in the focal point of the laser, resulting in a diminished excitation density. In such cases, ion emission lines become substantially less intensive and it is difficult to detect them. On the other hand, the molecule emission band intensity remains relatively strong.

Figure 3:
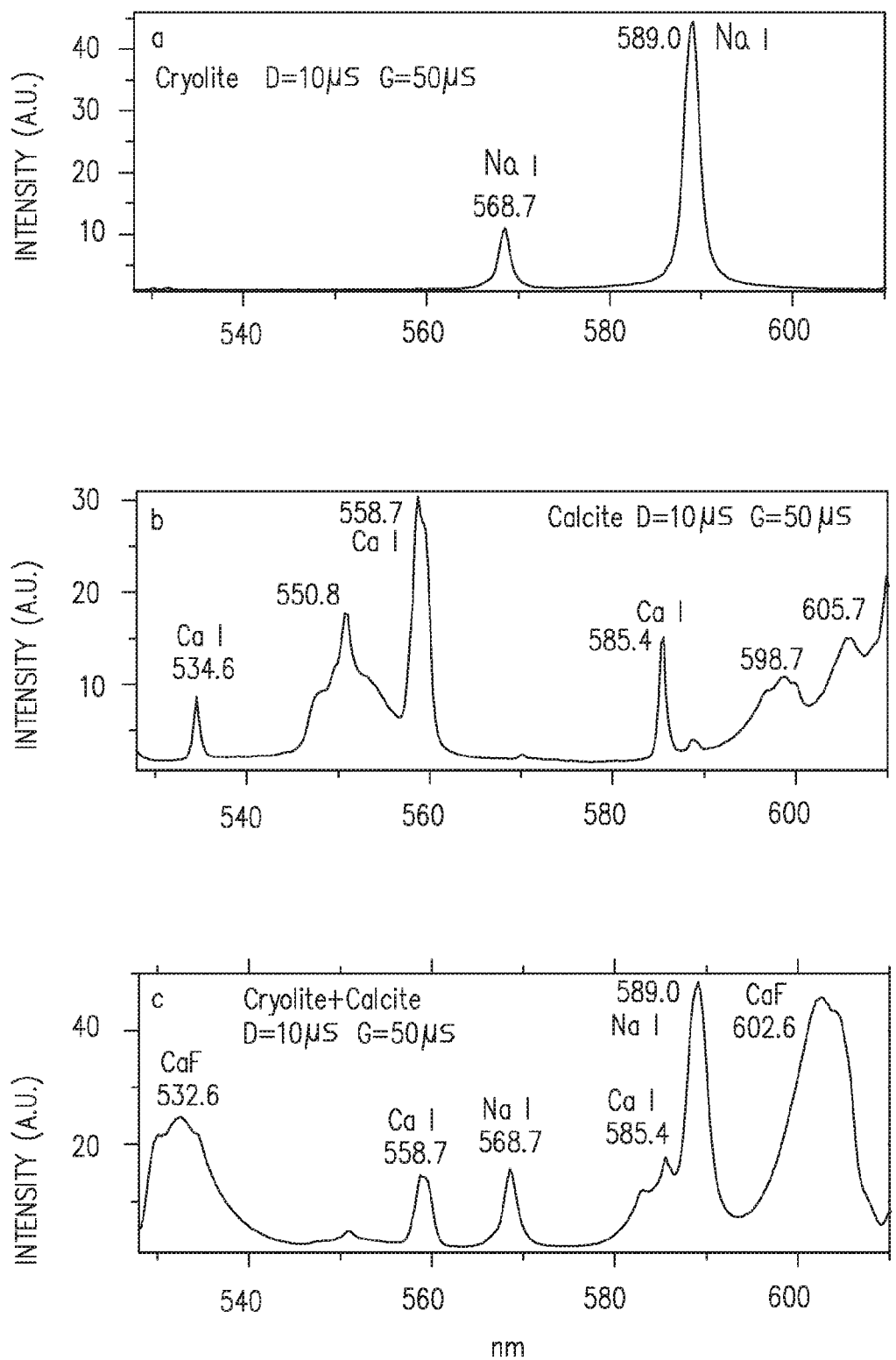

Several other fluorine and calcium bearing minerals have been studied, with lower fluorine content compared to fluorite $CaF_2$, such as magmatic fluorapatite $Ca_5(PO_4)_3F$, sedimentary carbonate apatite (francolite) $Ca_5(PO_4,CO_3)_3$ (F,OH) and apophyllite $KCa_4Si_8O_{20}F \times 8H_2O$. All of those minerals demonstrate CaF molecular emission bands in their breakdown spectra. It is also possible to use molecular emission bands to analyze minerals that do not contain both calcium and fluorine. For example, a calcium bearing mineral without fluorine, calcite $CaCO_3$, and a fluorine bearing mineral without calcium, cryolite $Na_3AlF_6$, separately do not have such emissions (FIGS. 3a, 3b), but they appear in their mechanical mixture (FIG. 3c).

Figure 4:
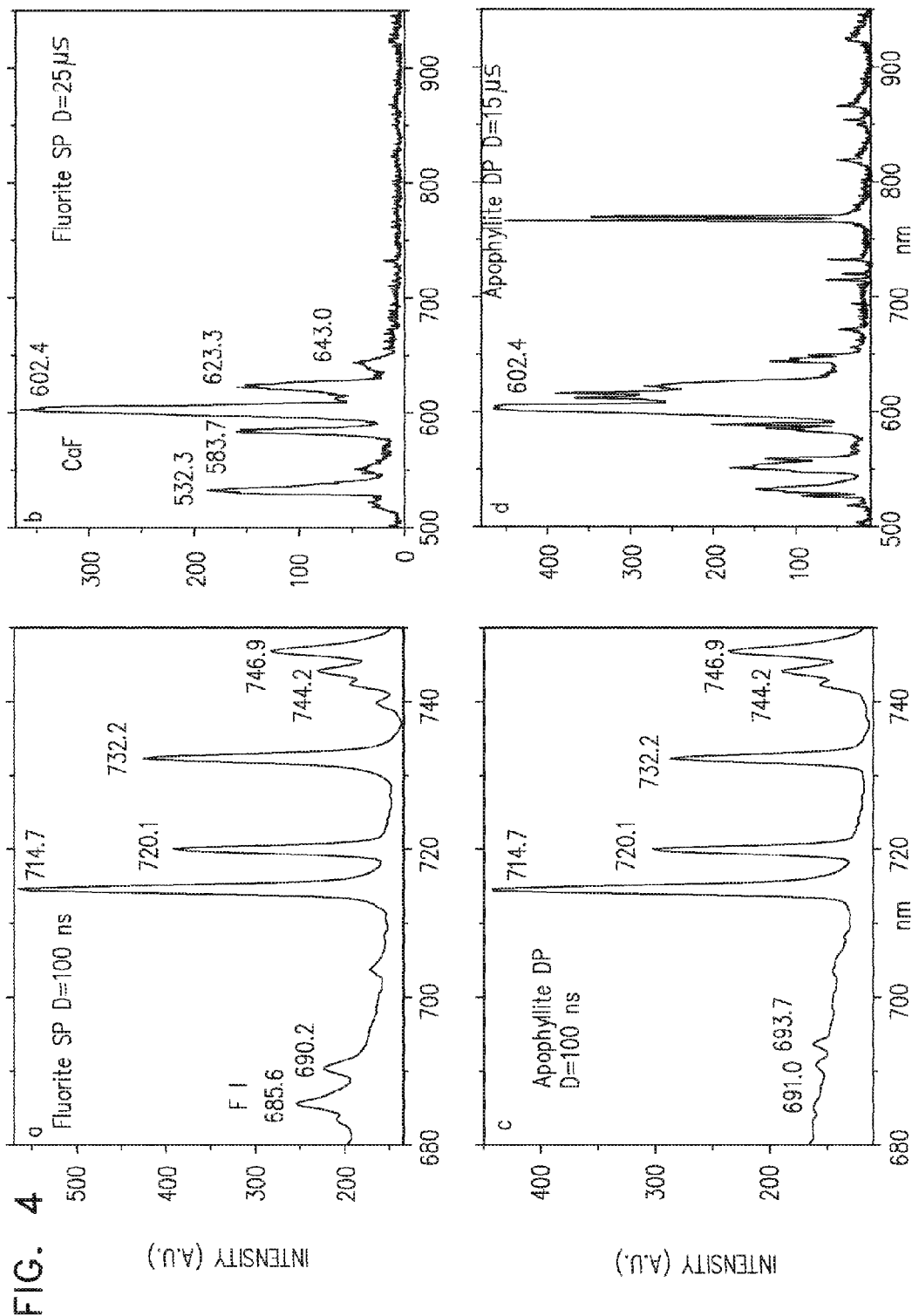

FIG. 4 shows a comparison between molecular CaF and ion F I DP LIBS sensitivity. Two minerals have been used, fluorite $CaF_2$ comprising approximately 50% fluorine and apophyllite $KCa_4Si_8O_{20}F \times 8H_2O$ comprising approximately 2% fluorine. The industrial Avantes spectrometer used in this experiment was constructed specifically for visible range detection and has similar spectral sensitivity in the emission range of CaF molecule and F I and Cl I ions (525-850 nm). The strongest F I emission lines at 685.6 and 690.2 nm may be seen in fluorite emission spectra with minimal delay time of 100 ns (FIG. 4a). Molecular emission of CaF was measured with delay time of 25 µs because with shorter delays the spectrometer was saturated. Even in this mode, the CaF strongest band intensity near 603 nm is approximately 6 times more intensive than the strongest F I ion line at 685.6 nm. The signal area difference is orders of magnitude larger (FIG. 4b). It was found that ion and molecular emissions become stronger in DP compared to SP LIBS, by 4 and 10 times, respectively. Thus the sensitivity difference becomes substantially larger in DP mode.

Double Pulse (DP) Laser Induced Plasma (LIP) spectra of apophyllite are presented in FIGS. 4c and 4d. FIG. 4c presents a spectrum detected with a delay time (D) of 100 ns, most suitable for detection of short-lived ion line emissions. It can be seen that the strongest lines of F I, which are the most suitable for fluorine detection in air, are not visible and, consequently, F may not be detected. FIG. 4d presents a spectrum detected with D=15 µs, which is most suitable for molecular emission detection because of their relatively long plasma life. After such a delay, the ion line emissions are mostly quenched. The band emission of the CaF molecule is clearly seen, especially the strongest band peaking at 602.4 nm. Thus the presence of 2% fluorine is detected by CaF molecule emission, while it is not detected by F I emission lines. Based on the signal to noise (S/N) ratio, a fluorine content of approximately 0.05-0.2%/o may be detected by molecular emission.

Figure 5:
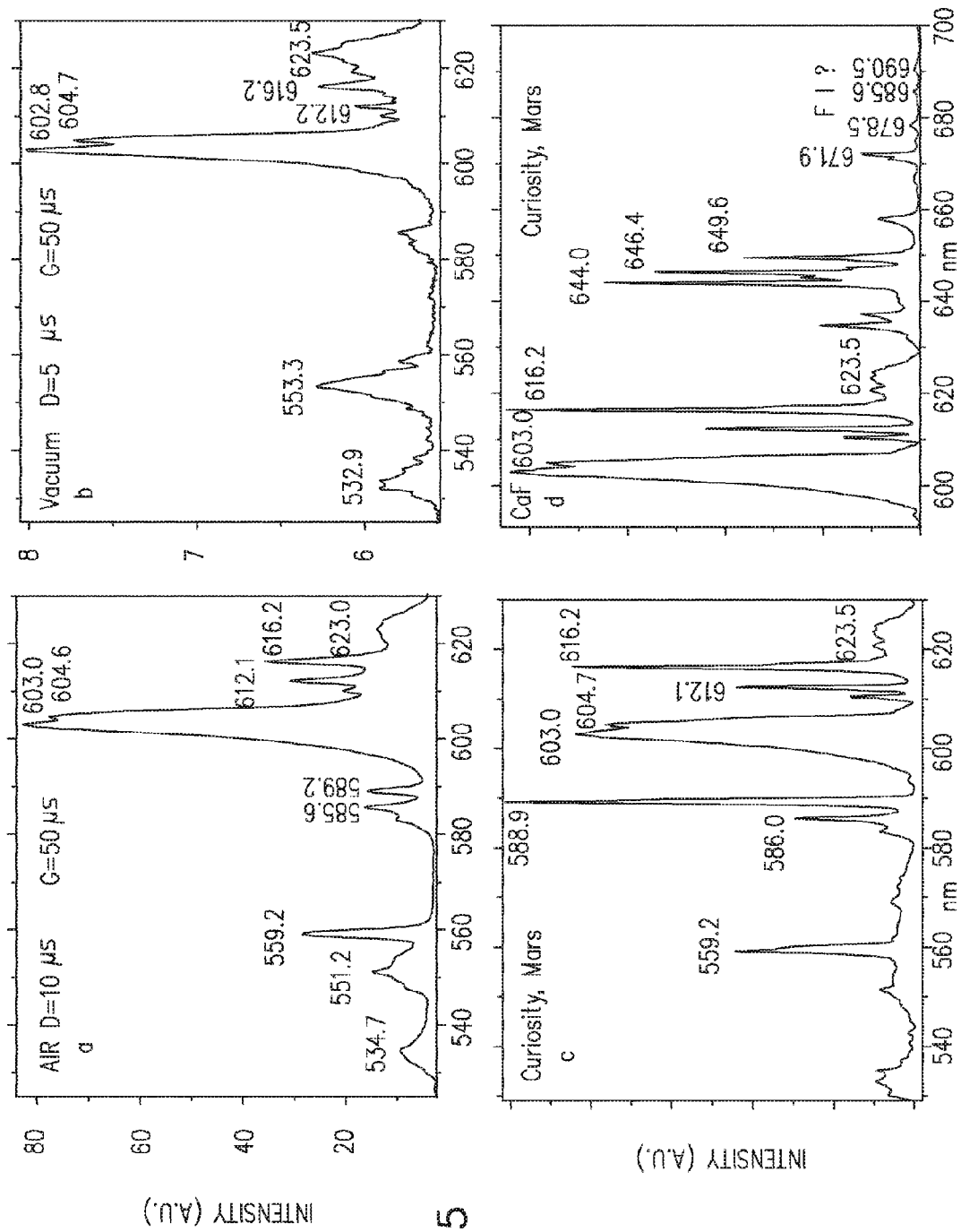

On Aug. 6, 2012, the Mars Science Laboratory rover, Curiosity, successfully touched down on the surface of Mars. Curiosity is equipped with the ChemCam device which includes a LIBS instrument, the first such instrument to be used on a planetary mission. At least 20 ChemCam observations contain bands ascribable to CaF molecular emission. FIG. 5 shows a comparison of the emission spectrum in fluorapatite $(Ca_5(PO_4)_3F)$ in air (FIG. 5a), in a vacuum chamber imitating Mars' atmospheric pressure (FIG. 5b) and the bands detected by the Curiosity ChemCam device (FIG. 5c). The characteristic bands for CaF molecular emission (623, 603, 585, 532 nm) are visible in all of these spectra. The total similarity in these bands' spectral positions and shapes, including the intensity ratios, enables their definite identification as CaF bands. This is the first reported detection of fluorine on Mars (Forni). The lines at 685 and 690 nm evidently belonging to F I ions are very weak, demonstrating once again the superior sensitivity using CaF molecules emission for fluorine detection (FIG. 5d).

Example 2—BaF and MgF

Figure 6:
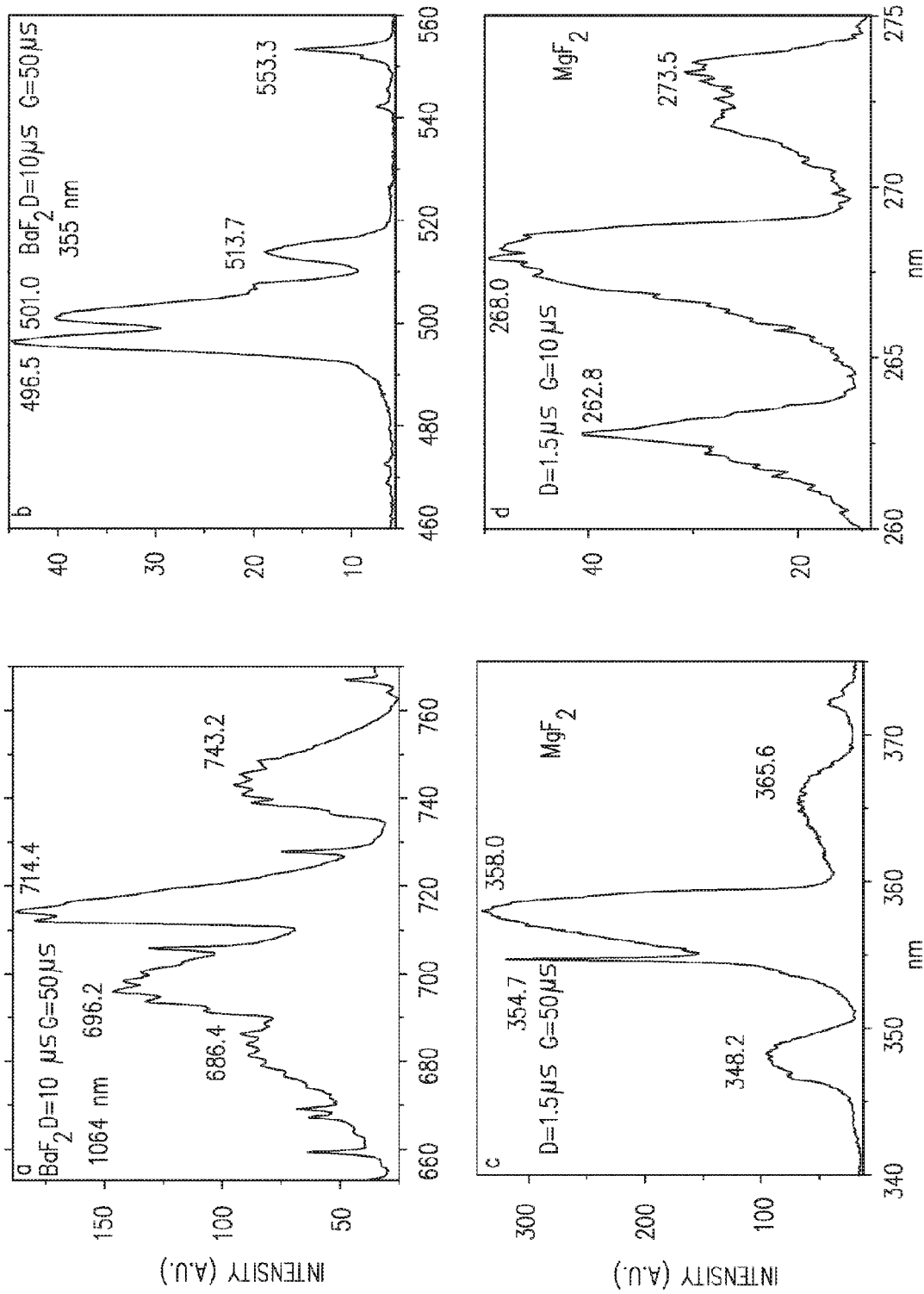

Compounds of fluorine with Ba and Mg were also studied. Plasma of BaF$_2$ excited by IR laser beam (first harmonic of Nd:YAG laser at 1064 nm) exhibited several long lived broad emission bands with vibrational structure peaking at 686.4, 696.2, 714.4 and 743.2 nm, ascribable to the $^2\Sigma$-$^2\Sigma$ extreme red system of the BaF molecule (FIG. 6a). Plasma of BaF$_2$ excited by UV laser beam (third harmonic of Nd:YAG laser at 355 nm) exhibited in addition the green system peaking at 496.5, 501.0 and 513.7 nm (FIG. 6b) ascribed to the $^2\Pi$-$^2\Sigma$ system (Jenkins, 1932). Plasma of MgF$_2$ excited by both IR and UV laser beams contain relatively broad emission bands in UV spectral range. The first one peaking at 348.2, 358.0 and 365.6 nm (FIG. 6c) is connected to $^2\Pi$-$^2\Sigma$ system of MgF molecule emission, while the second peaking at 262.8, 268.0 and 273.5 nm belongs (FIG. 6d) to $^2\Sigma$-$^2\Sigma$ system of MgF molecule emission (Jenkins, 1934).

Example 3—CaCl

Figure 7:
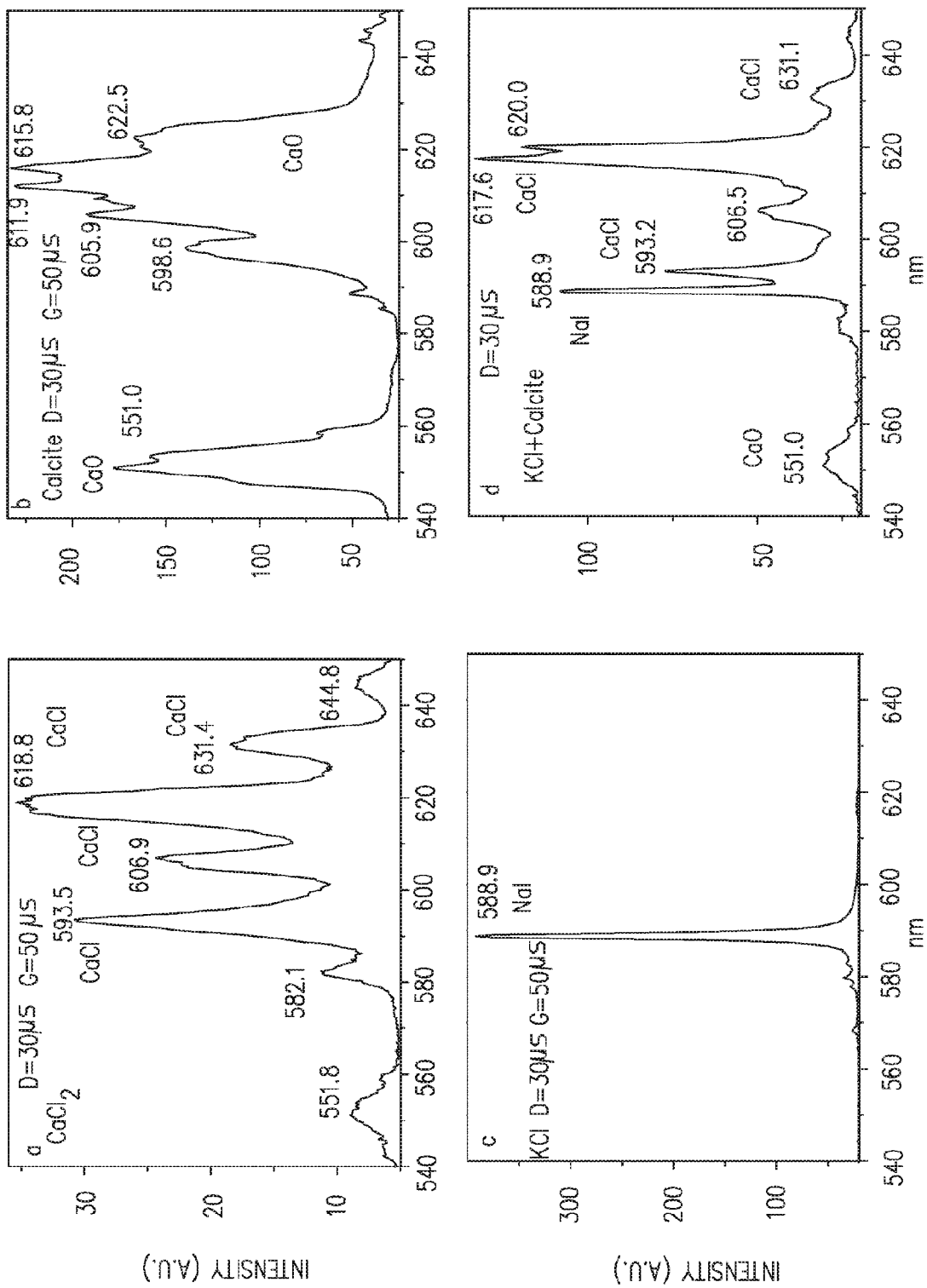

Molecular emission of CaCl was studied using pure CaCl$_2$ because minerals containing both Ca and Cl are relatively rare. Broad long lived emission bands were found in the orange part of the spectrum with vibrational maxima at 593.5 of CaCl orange system and at 606.9, 618.8 and 631.4 nm belonging to red system of CaCl (FIG. 7a). Those emissions are connected to transitions from B $^2\Sigma^+$ and A $^2\Pi$ levels to X$^2\Sigma^+$ ground level (Berg). The connection with CaCl molecule was confirmed by the fact that calcium bearing calcite CaCO$_3$ (FIG. 7b) and chlorine bearing sylvite KCl (FIG. 7c) do not contain such bands in their breakdown spectra, while their mixture exhibits narrow bands peaking at 593.2, 606.5, 617.6, 620.0 and 630.1 nm (FIG. 7d). The bands peaking at 551 and 615 nm in the calcite breakdown spectrum are connected to green and orange emission bands of CaO molecule (Pearse). Those bands have long lifetime and appear in all calcium bearing minerals.

Figure 8:
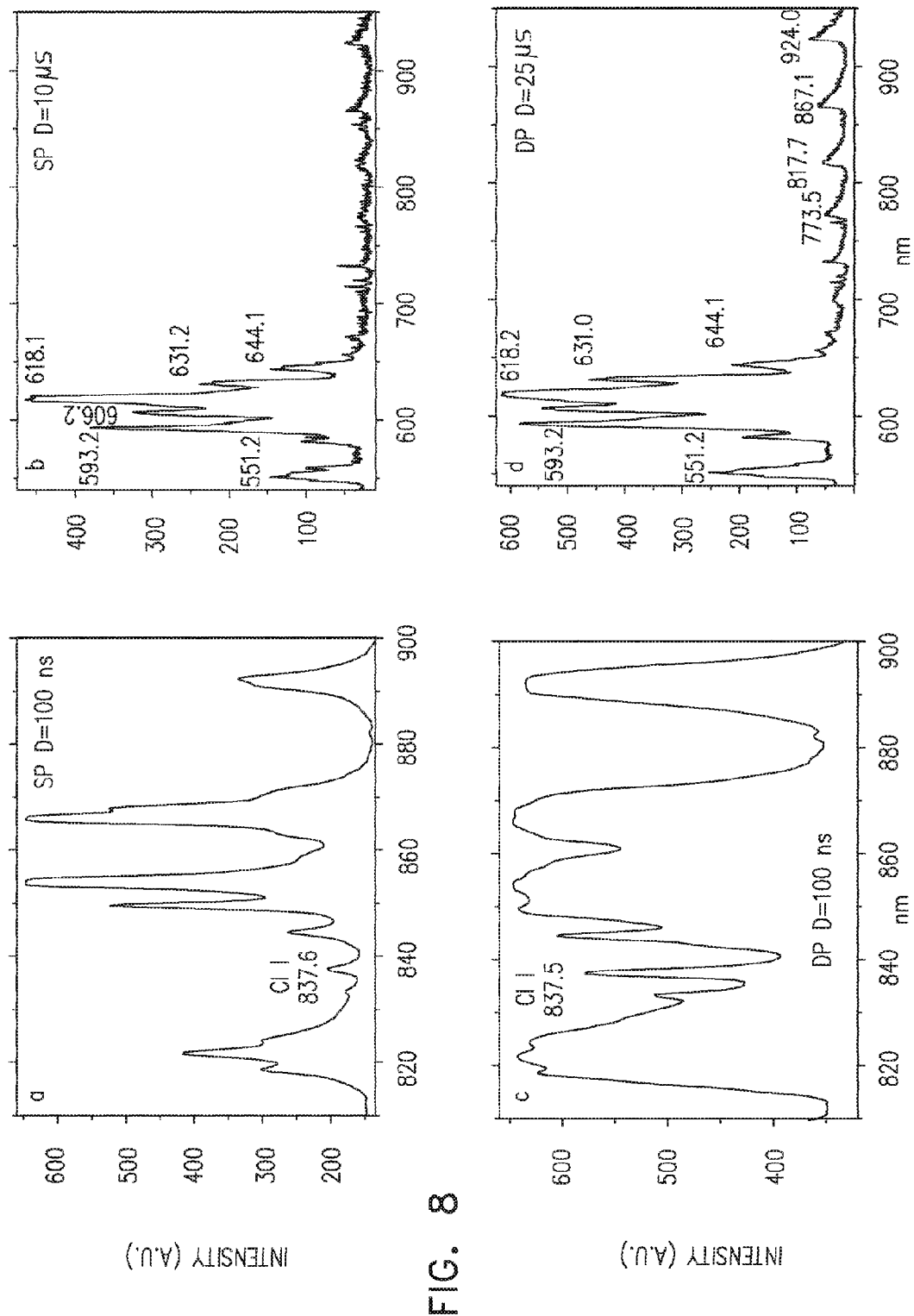

FIG. 8 shows a comparison between molecular CaCl and ion Cl I LIBS sensitivity in CaCl$_2$ comprising approximately 64% chlorine. The strongest Cl I emission line at 837.6 nm is seen in SP emission spectrum with D=100 ns (FIG. 8a). Molecular emission of CaCl$_2$ was measured with D=10 μs, and the main band at 618 nm intensity is approximately ten times higher compared to Cl I ion emission. The signal area difference is one order of magnitude larger (FIG. 8b). In DP mode the Cl I ion emission intensity is approximately 5 times higher than in SP mode (FIG. 8c) For molecular CaCl, the DP emission was measured after delay of 25 is because with shorter delays the spectrometer was saturated. Even in this mode, the CaCl strongest band intensity near 618 nm is approximately 3 times more intensive than the strongest Cl I ion line at 685.6 nm. The signal area difference is approximately 40 fold (FIG. 8d). With a smaller Cl content, when the spectrometer will not be saturated after delay of 5-10 μs, the CaCl signal will be 5-10 times stronger than after 25 μs. Thus the difference between ion Cl I and molecular CaCl emissions under DP conditions will be 200-400. It may be concluded, that molecular CaCl emission is about 100 times more effective for Cl detection than ion Cl I emission under SP conditions and 200-400 times more effective in DP mode.

Example 4—MgCl and SrCl

Figure 9:
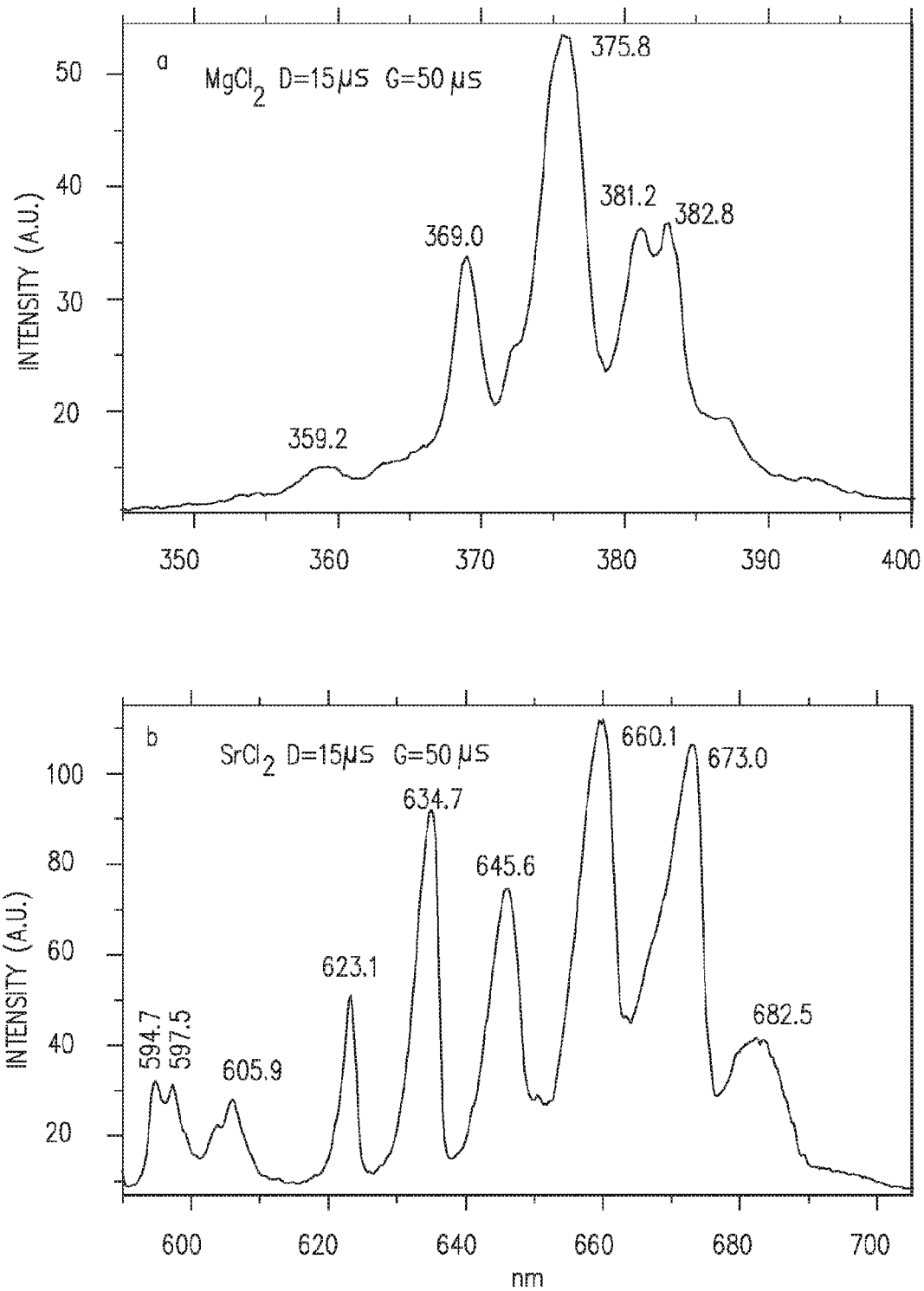

Compounds of chlorine with Mg and Sr were also studied. Synthetic compounds MgCl$_2$ and SrCl$_2$ were used. Plasma of MgCl$_2$ excited by IR laser beam (1064 nm) exhibited several long lived broad emission bands with vibrational structure peaking at 359.2, 369.0, 375.8, 381.2 and 382.8 nm (FIG. 9a). These peaks can be ascribed to the A $^2$ Π-X $^2\Sigma$ system of MgCl (Pearse). Plasma of SrCl$_2$ excited by IR laser beam contained relatively broad emission bands in the red spectral range peaking at 594.7, 597.5, 605.9, 623.1, 634.7, 645.6, 660.1, 673.0 and 682.5 nm (FIG. 9b) ascribed to red B $^2\Sigma$-X $^2\Sigma$ system of SrCl (Pearse). The spectrum is very similar to that previously reported (Mao), where the bands near 600 nm have been ascribed to SrO emission.

Example 5—CaBr

Figure 10:
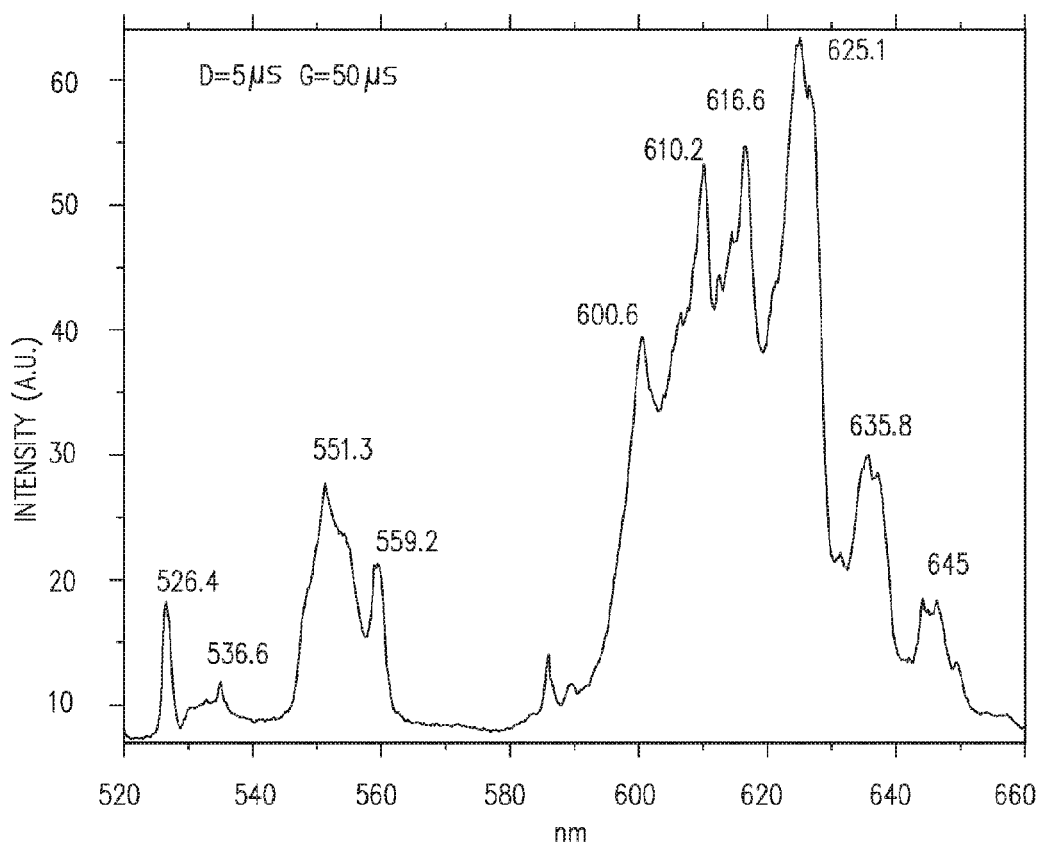

FIG. 10 presents SP LIBS emissions of synthetic compound CaBr$_2$ with a delay time of 5 μs and a gate width of 50 μs. The red system of CaBr peaking at 625-628 nm spectral region (Pearse) is clearly detected.

Example 6—LaO

Figure 11:
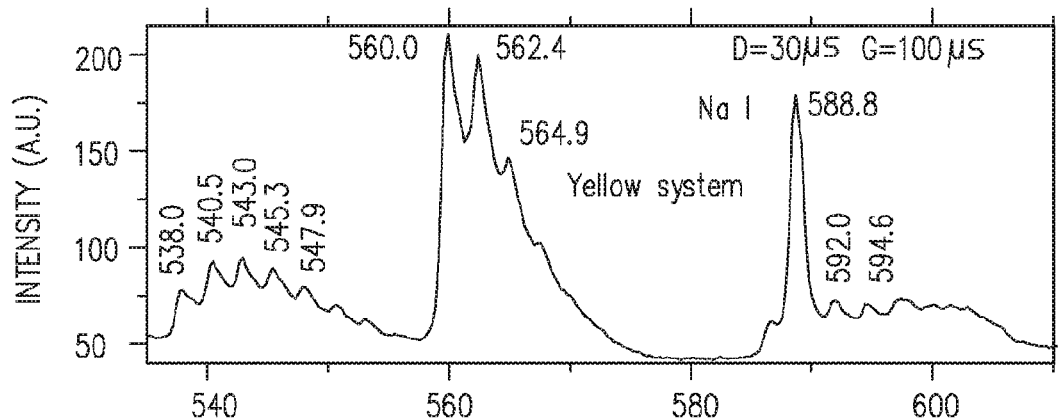
Figure 11:
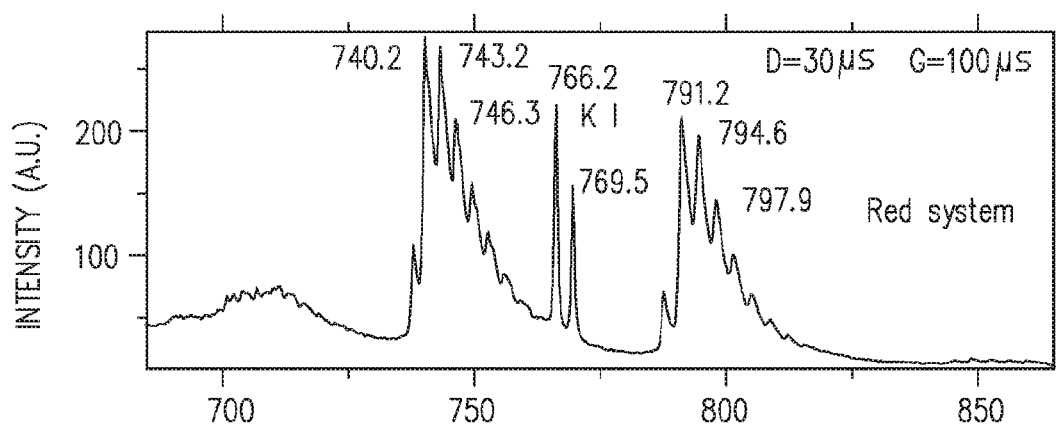
Figure 11:
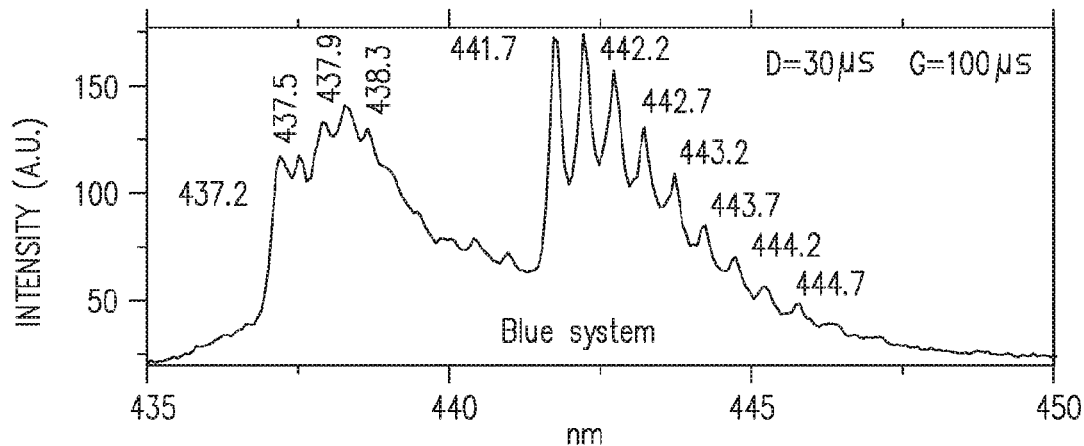
Figure 12:
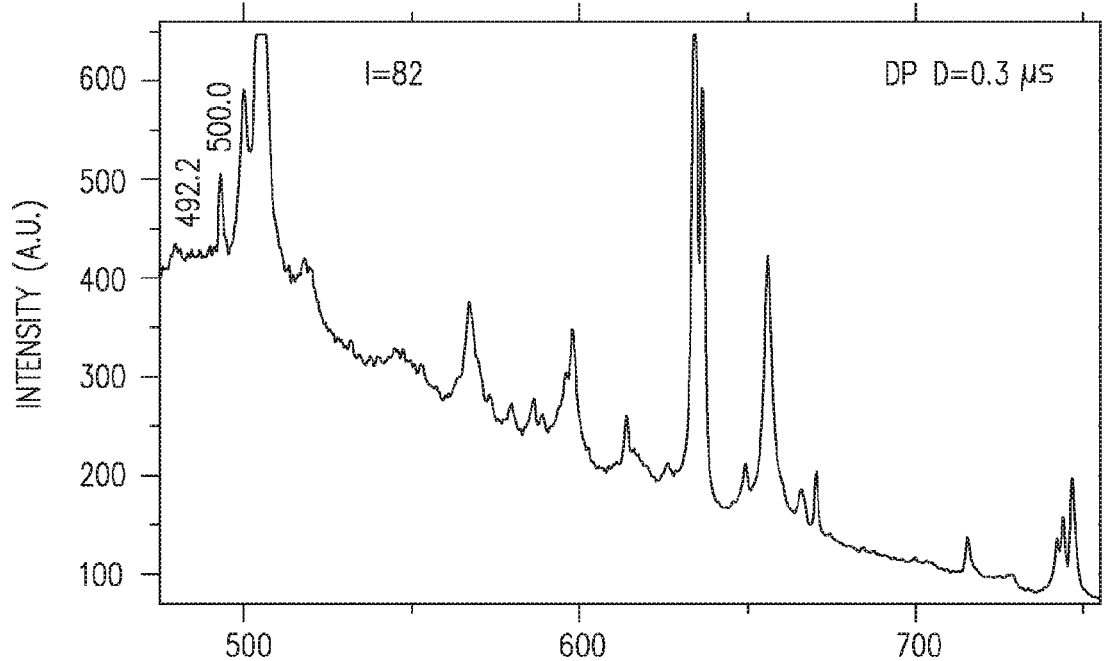
Figure 12:
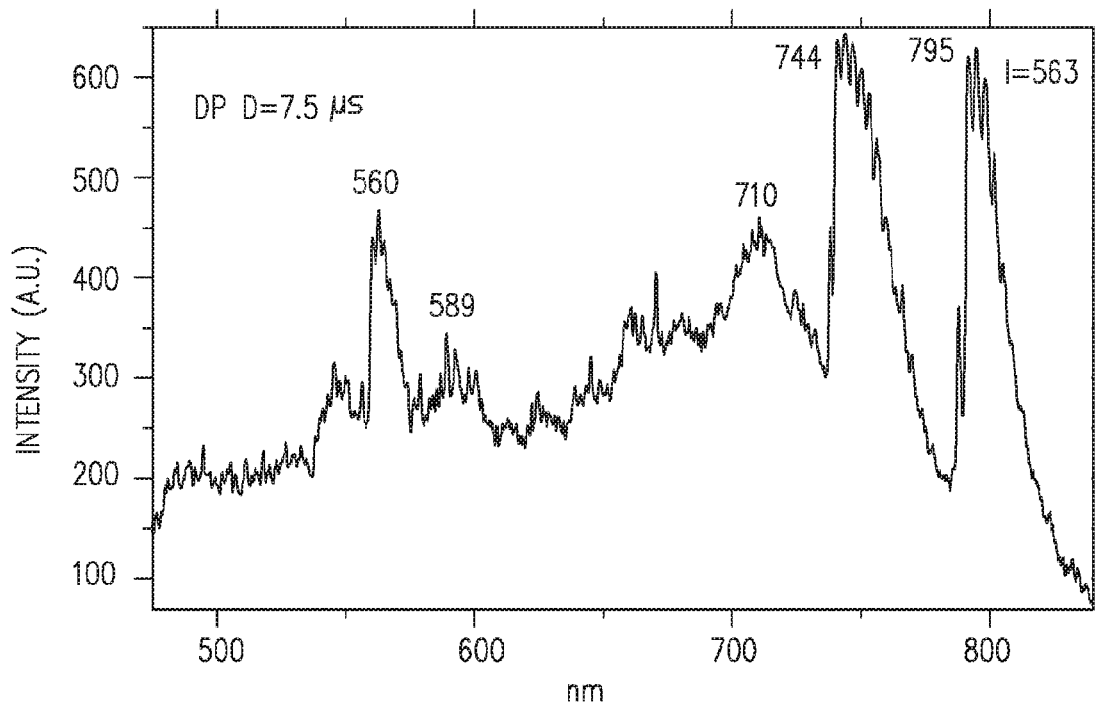

FIG. 11 presents emission spectra of rare-earth bearing mineral bastneasite (Ce,La)CO$_3$(F,OH), which is one of the main industrial minerals for rare-earth elements production. Three well-known LaO yellow, red and blue systems are clearly detected (Pearse). FIG. 12 presents a comparison between molecular LaO measured with D=7.5 μs and ion La I measured with D=300 ns emission lines sensitivity in bastneasite. The strongest La I emission lines at 492.2 and 500.0 nm have been compared with molecular red system of LaO and it was found that the latter is approximately seven times more intensive in DP mode. The signal area difference is approximately 200 fold. In SP mode, the LaO band was weak but detectable. The La I ion line was not detected.

Example 7—YO

Figure 13:
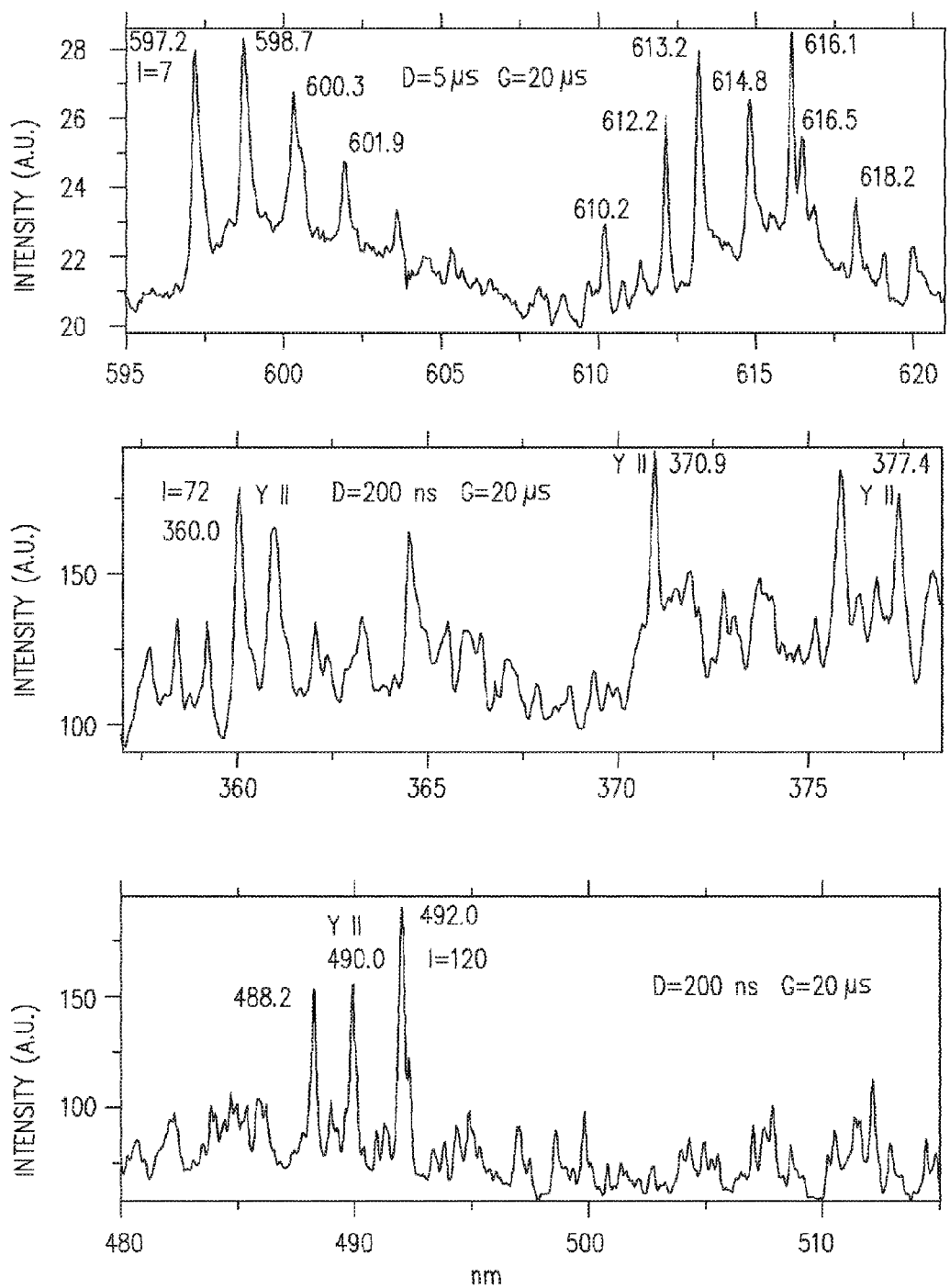

FIG. 13 presents emission spectra of industrial rare earth mineral xenotime YPO$_4$. Very strong lines peaking at 616.5, 614.8, 613.2, 600.3, 598.7 and 597.2 nm (FIG. 13, top panel) belong to the orange system of the YO molecule (Pearse). The strongest Y II emission lines at 360.0, 370.9, 377.4 (FIG. 12, middle panel) and 490.2 nm (FIG. 13, lower panel) have been compared with YO emission bands intensities. In this case it is appears that the lines intensities are 10-15 times stronger compared to the molecular ones. Nevertheless, the areas comparison is favorable toward molecular bands.

Example 8—Ca$_x$B$_y$O$_z$

Figure 14:
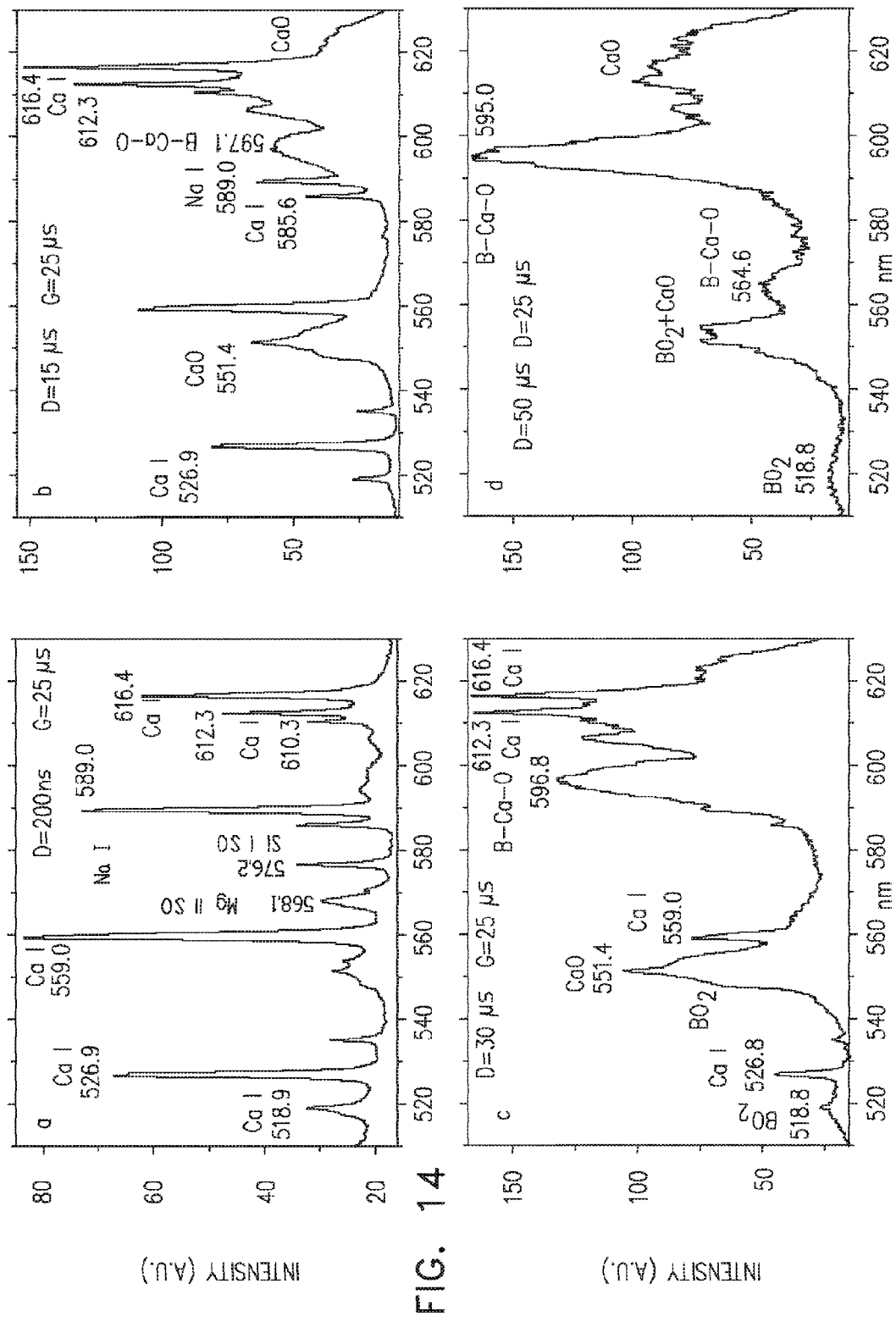

FIG. 14 presents SP LIBS emission spectra of the mineral danburite CaB$_2$(SiO$_4$)$_2$. With a small delay time of 200 ns the major elements Ca I and Si I may be detected, accompanied by Na I and Mg II impurities (FIG. 14a). Si I and Mg II are detected by their second order (SO) lines, while their first order lines have emissions peaking at approximately 284 and 288 nm, respectively. After a delay time of 15 μs, the line intensity is lower, and the molecular bands become visible. CaO bands are observed at 550 and 620 nm, and an unidentified band peaks at 597 nm (FIG. 14b). The latter band has not been observed or interpreted before, neither in LIBS nor in any other kind of plasma spectrometry, at least according to our knowledge. After a delay time of 30 μs, these molecular bands are even more clear (FIG. 14c), while a band at 519 nm becomes visible, which band belongs to the BO$_2$ molecule (Pearse). As in the case of CaF and CaCl, this band was previously observed in arc plasma, but has not found in LIBS according to our knowledge. After an even longer delay time of 50 μs, an additional unidentified band at 565 nm is observed.

The bands at 565 and 597 nm were determined to originate from a complex of calcium, boron and oxygen as follows: The emission spectrum of pure boron in air was measured and the known bands for BO and $BO_2$ were observed, while the bands at 565 and 597 nm were not observed. Next, mixtures of boron bearing and calcium bearing minerals were prepared and studied. Their emissions spectra in air exhibit strong bands at 565 and 597 nm. At the next step, mixtures of boron with calcium and without oxygen were studied in an oxygen free atmosphere. Under these conditions, the bands at 565 and 597 nm were not observed. Thus, it was determined that those bands belong to molecules containing boron, calcium and oxygen. The exact molecular composition was not determined. It was noted that boron bearing molecules dominate the spectrum with a delay time of 50 μs, indicating that they have an even longer plasma life than CaO molecules.

Example 9—$Mg_xB_yO_z$

Figure 15:
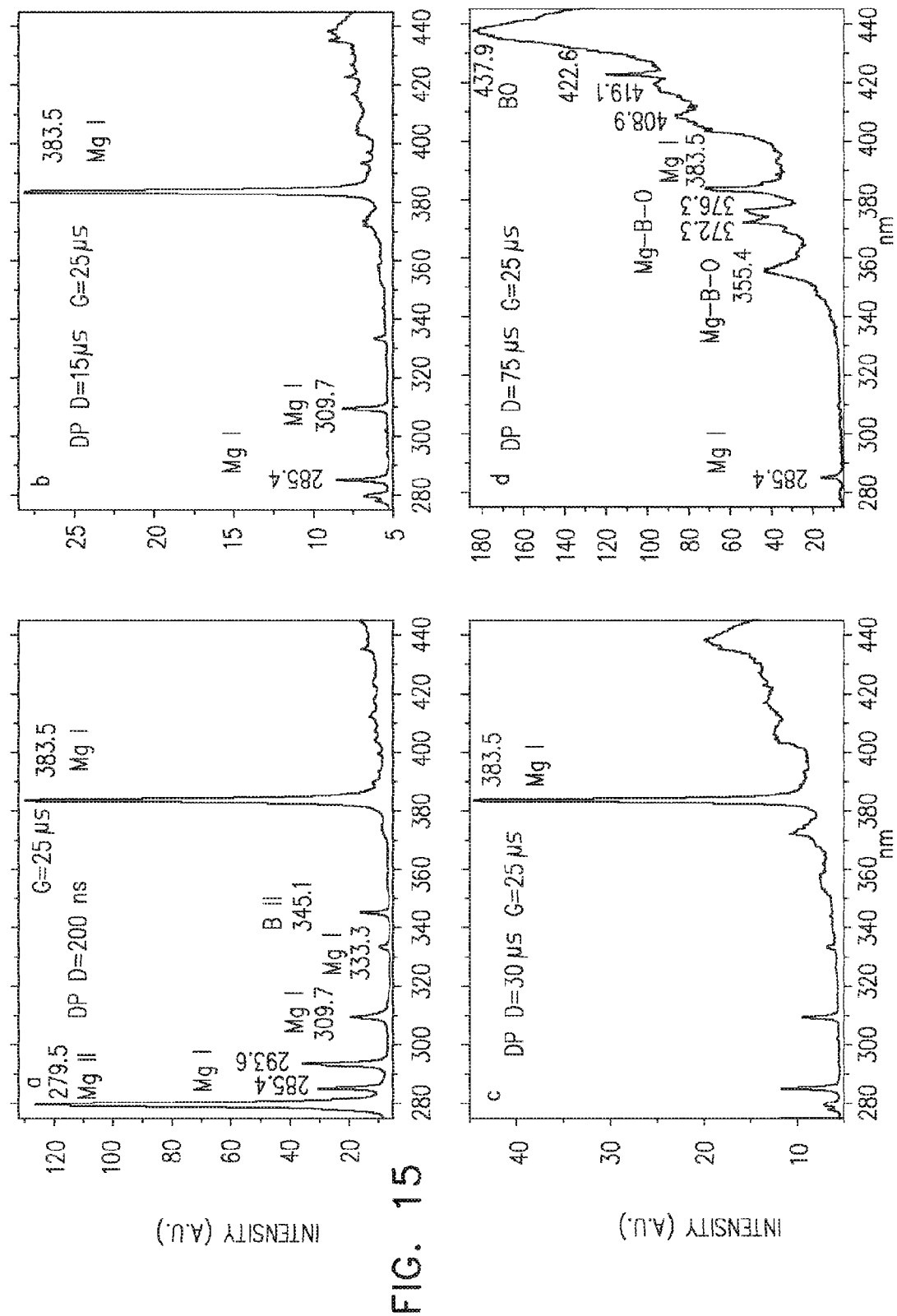

FIG. 15 presents DP LIBS emission spectra of the mineral boracite $Mg_3B_7O_3Cl$. With a small delay time of 200 ns the major elements Mg I, Mg II and B II may be detected (FIG. 15a). It is noted that the boron elemental peak is much weaker than the magnesium peaks. After a delay times of 15 μs (FIG. 15b), 30 μs (FIG. 15c) and 75 μs (FIG. 15d), the line intensity progressively decreases, and the molecular bands become more visible. The band observed at 438 nm is from BO. The bands at 355, 368, 372 and 376 nm have not been observed or interpreted before, neither in LIBS nor in any other kind of plasma spectrometry, at least according to our knowledge.

These bands were determined to originate from a complex of magnesium, boron and oxygen as follows: The emission spectrum of pure boron in air was measured and the known bands for BO and $BO_2$ were observed, while the bands at 355, 368, 372 and 376 nm were not observed. Next, mixtures of boron bearing and magnesium bearing minerals were prepared and studied. Their emissions spectra in air exhibit strong bands at 355, 368, 372 and 376 nm. At the next step, mixtures of boron with magnesium and without oxygen were studied in an oxygen free atmosphere. Under these conditions, the bands at 355, 368, 372 and 376 nm were not observed. Thus, it was determined that those bands belong to molecules containing boron, magnesium and oxygen. The exact molecular composition was not determined.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to a person of skill in the art upon reading the foregoing description and which are not in the prior art.

REFERENCES

The contents of the following publications are incorporated by reference herein in their entirety:
Berg et al. Chem Phys Lett. (1996), 257:351-355.
Cremers and Radziemski, Handbook of Laser-Induced Breakdown spectroscopy, Wiley, 2006.
Darji et al., Pramana—J Phys. (1987), 29:279-284
Forni et al., Lunar and Planetary Science Conference, Geophys Res-Plan (2014).
Forni et al. Nature (2014), In Press.
Jaffe, H. W., Am. Mineralogist (1949), 34:667-674.
Jenkins and Harvey, Phys Rev (1932), 39:922-931.
Jenkins and Grienfeld, Phys Rev (1934), 45:229-233.
Mao et al. Spectrochimica Acta B (2011), 66:767-775.
Miziolek, et al. Laser Induced Breakdown Spectroscopy: Fundamentals and Applications. Cambridge, 2006.
NIST Atomic Spectra Database Lines From: http://physics.nist.gov/PhysRefData/ASD/lines_form.html
Oujja et al. Phys. Rev. A (2010), 81:043841-043847.
Pearse and Gaydon, The Identification of the Molecular Spectra, Wiley: New York, 1965.
Pelegrini et al., Brazilian J. Phys. (2005) 35:950-956).
Peterson and Jaffe, US Dept. of the Interior, Bur. Mines Bull. (1953) 524
R. Russo et al. Spectrochimica Acta Part B (2011), 66:99-104.
Smith et al., "Atomic spectral line database built from atomic data files" from R. L. Kurucz' CD-ROM 23, http://www.pmp.uni-hannover.de/cgi-bin/ssi/test/kurucz/sekur.html

The invention claimed is:

1. A method for detecting an element in a sample, the method comprising:
providing a laser-induced breakdown spectroscopy (LIES) system including:
a first laser;
a second laser;
a spectrometer; and
a detector;
delivering a first pulse from said first laser to a surface of said sample;
thereafter delivering a second pulse from said second laser to said surface of said sample; and
detecting molecular emissions of a molecule comprising said element.

2. The method according to claim 1, wherein said element is a halogen.

3. The method according to claim 2, wherein said element is F.

4. The method according to claim 3, wherein said molecule is selected from CaF, MgF, BaF and SrF.

5. The method according to claim 2, wherein said element is Cl.

6. The method according to claim 5, wherein said molecule is selected from CaCl, MgCl, SrCl and BaCl.

7. The method according to claim 2, wherein said element is Br.

8. The method according to claim 7, wherein said molecule is CaBr.

9. The method according to claim 2, wherein said element is I.

10. The method according to claim 9, wherein said molecule is CaI.

11. The method according to claim 1, wherein said element is a rare-earth element.

12. The method according to claim 11, wherein said element is selected from Y, La and Th.

13. The method according to claim 12, wherein said molecule is selected from YO and LaO.

14. The method according to claim 1, wherein said element is boron.

15. The method according to claim 14, wherein said molecule is selected from BO, $BO_2$, a molecule consisting of boron, calcium and oxygen, and a molecule consisting of boron, magnesium and oxygen.

16. The method according to claim 1, wherein the time between said emitting a first pulse and said emitting a second pulse is 300-1000 ns.

17. The method according to claim 1, wherein both of said first laser and said second laser are Nd:YAG lasers.

18. The method according to claim 1, wherein said detecting begins after a delay time following said emitting a second pulse.

19. The method according to claim 18, wherein said delay time is between 5 and 75 µs.

20. The method according to claim 19, wherein said delay time is between 5 and 50 µs.

\* \* \* \* \*